United States Patent
Hull et al.

(10) Patent No.: US 9,936,715 B2
(45) Date of Patent: Apr. 10, 2018

(54) COMPOSITIONS AND METHODS FOR LOWERING COUNTS OF PATHOGENIC MICROORGANISMS IN FOOD PRODUCTS

(71) Applicant: IsoAge Technologies LLC, Athens, GA (US)

(72) Inventors: Richard Hull, Athens, GA (US); Mo Toledo, Hull, GA (US); Romeo Toledo, Hull, GA (US)

(73) Assignee: ISOAGE TECHNOLOGIES LLC, Athens, GA (US)

( * ) Notice: Subject to any disclaimer, the term of this patent is extended or adjusted under 35 U.S.C. 154(b) by 0 days.

(21) Appl. No.: 15/049,724

(22) Filed: Feb. 22, 2016

(65) Prior Publication Data

US 2016/0165908 A1 Jun. 16, 2016

Related U.S. Application Data

(62) Division of application No. 13/770,705, filed on Feb. 19, 2013, now Pat. No. 9,265,266.

(60) Provisional application No. 61/599,732, filed on Feb. 16, 2012.

(51) Int. Cl.

| | | |
|---|---|---|
| *A01N 37/02* | (2006.01) | |
| *A01N 37/36* | (2006.01) | |
| *A01N 37/42* | (2006.01) | |
| *A23B 4/20* | (2006.01) | |
| *A23B 4/14* | (2006.01) | |
| *A23B 4/12* | (2006.01) | |
| *A23L 3/3472* | (2006.01) | |
| *A23L 3/3517* | (2006.01) | |
| *A01N 25/02* | (2006.01) | |
| *A01N 31/02* | (2006.01) | |
| *A01N 31/08* | (2006.01) | |
| *A23L 13/40* | (2016.01) | |
| *A23L 13/70* | (2016.01) | |

(52) U.S. Cl.
CPC .............. *A23B 4/20* (2013.01); *A01N 25/02* (2013.01); *A01N 31/02* (2013.01); *A01N 31/08* (2013.01); *A01N 37/02* (2013.01); *A01N 37/36* (2013.01); *A01N 37/42* (2013.01); *A23B 4/12* (2013.01); *A23B 4/14* (2013.01); *A23L 3/3472* (2013.01); *A23L 3/3517* (2013.01); *A23L 13/428* (2016.08); *A23L 13/72* (2016.08); *A23V 2002/00* (2013.01)

(58) Field of Classification Search
CPC ......... A01N 37/02; A01N 37/36; A01N 37/42
See application file for complete search history.

(56) References Cited

U.S. PATENT DOCUMENTS

| | | |
|---|---|---|
| 8,445,419 B2 | 5/2013 | Timothy et al. |
| 2003/0228402 A1 | 12/2003 | Franklin et al. |
| 2007/0059423 A1 | 3/2007 | Toledo et al. |

OTHER PUBLICATIONS

E.C. Friedly et al., "In vitro Antilisterial Effects of Citrus Oil Fractions in Combination with Organic Acids", Journal of Food Science, vol. 74, No. 2, Mar. 1, 2009, pp. M67-M72.
Burt, S., "Essential Oils: Their Antibacterial Properties and Potential Applications in Foods—A Review", International Journal of Food Microbiology, vol. 94, No. 3, Jan. 1, 2004, pp. 223-253.
Extended European Search Report from European Patent Application No. 13749441.5, dated Sep. 22, 2015.
Mohan et al. "The antimicrobial efficacies of novel organic acids as single antimicrobial intervention for the control of *Escherichia coli* O 157:H7 in inoculated beef trimmings", Arkansas animal science department report 2011 (Univ of Arkansas, Fayetteville, Arkansas; 2011) pp. 108-111, ed. Kreider DL. Retrieved from http://arkansasagnewuark.edu/597-26.pdf.
PCT International Search Report for PCT/US13/26704 dated Apr. 29, 2013.
Anjana et al., Antimicrobial Agents and Chemotherapy, Oct. 4, 2010.

*Primary Examiner* — Zohreh A Fay
(74) *Attorney, Agent, or Firm* — Stroock & Stroock & Lavan, LLP

(57) ABSTRACT

Compositions and methods for lowering counts of pathogenic microorganisms in food products such as ready to eat meat and poultry products are disclosed. In various embodiments, the compositions and methods comprise antimicrobial compositions with one or more essential oils added.

7 Claims, 13 Drawing Sheets

COMPOSITIONS AND METHODS FOR LOWERING COUNTS OF PATHOGENIC MICROORGANISMS IN FOOD PRODUCTS

CROSS REFERENCE TO RELATED APPLICATIONS

This application is a divisional of, and claims priority under 35 U.S.C. § 120 to, U.S. patent application Ser. No. 13/770,705, filed Feb. 19, 2013, which claims the benefit of, and priority to, U.S. Provisional Application No. 61/599,732, filed Feb. 16, 2012, each of which is incorporated herein by reference in its entirety.

BACKGROUND

Food poisoning by certain microorganisms poses a threat to consumers. For example, *Listeria monocytogenes* has emerged as a major source of foodborne illness, with a high rate of hospitalizations (88%) and fatality rate (20%). Listeriae are Gram positive, non-spore forming, motile, coccobacilli. *Listeria* are capable of growth over a temperature range of 1 to 45° C., making the organism a food safety concern in refrigerated foods, especially ready-to-eat (RTE) meat and poultry products.

Protecting the consumer from food poisoning hazards is a primary concern of food processors. RTE meat and poultry processors are required by the United States Department of Agriculture Food Safety and Inspection Service (USDA-FSIS) to establish controls to reduce the risk of certain foodborne illnesses. The USDA-FSIS enforces a "zero tolerance" policy for pathogens such as *Salmonella* spp., *E. coli* 0157:H7, and *L. monocytogenes* in RTE products.

Accordingly, there is a need in the art for compositions and methods for controlling microorganisms in RTE meat and poultry products.

SUMMARY

The invention relates to compositions and methods for lowering counts of pathogenic microorganisms in food products such as ready to eat meat and poultry products.

In one aspect, the invention provides a method of increasing antimicrobial activity of an antimicrobial composition for treating a meat product, comprising adding to the antimicrobial composition at least one essential oil.

In some embodiments, said adding further comprises adding to the antimicrobial composition approximately equal parts of a first essential oil component consisting essentially of 5-isopropyl-2methylphenol (Carvecrol), and a second essential oil component consisting essentially of 3,7-dimethylocta-1,6-dien-3-ol (Linalool), in amounts sufficient to yield concentrations of each essential oil component of about two micrograms per gram of meat product. In some embodiments, the antimicrobial composition to which the at least one essential oil is added comprises at least one organic acid. In some embodiments, the method further comprises adding caprylic acid to the antimicrobial composition containing the at least one essential oil.

In a related aspect, embodiments of the invention provide a composition for treating a meat product, comprising: a vinegar mixture, comprising approximately equal parts of concentrated buffered vinegar, comprising buffered vinegar that has been concentrated by evaporation to produce an elevated acetate concentration of about 34 to 38% acetate salts and a free acetic acid content of about 3.5 to 4.5% by weight and unconcentrated buffered vinegar; and at least one essential oil. In some embodiments, said at least one essential oil comprises an essential oil mixture comprising approximately equal parts of a first essential oil component consisting essentially of 5-isopropyl-2methylphenol (Carvecrol); and a second essential oil component consisting essentially of 3,7-dimethylocta-1,6-dien-3-ol (Linalool). In some embodiments, concentrations of essential oil components in the treated meat product are each about two micrograms per gram of meat product.

In some embodiments, the composition further comprises at least one additional organic acid. In some embodiments, the composition further comprises levulinic acid and malic acid, wherein the vinegar mixture, the levulinic acid, and the malic acid are in approximately equal parts. In some embodiments, the composition further comprises caprylic acid. In some embodiments, the composition further comprises a mixture of malic acid and its mineral salt in a ratio that raises the pH of the malic acid component in the mixture to about 5.2.

In another aspect, embodiments of the invention provide a composition for treating a meat product, comprising approximately equal parts of levulinic acid and malic acid; and at least one essential oil. In some embodiments, said at least one essential oil comprises an essential oil mixture comprising approximately equal parts of a first essential oil component consisting essentially of 5-isopropyl-2methylphenol (Carvecrol); and a second essential oil component consisting essentially of 3,7-dimethylocta-1,6-dien-3-ol (Linalool). In some embodiments, concentrations of essential oil components in the treated meat product are each about two micrograms per gram of meat product.

In some embodiments, the composition further comprises caprylic acid. In some embodiments, the composition further comprises a mixture of malic acid and its mineral salt in a ratio that raises the pH of the malic acid component in the mixture to about 5.2.

Additional features and advantages of the present invention are described further below. This summary section is meant merely to illustrate certain features of embodiments of the invention, and is not meant to limit the scope of the invention in any way. The failure to discuss a specific feature or embodiment of the invention, or the inclusion of one or more features in this summary section, should not be construed to limit the invention as claimed.

BRIEF DESCRIPTION OF THE DRAWINGS

The foregoing summary, as well as the following detailed description of the preferred embodiments of the application, will be better understood when read in conjunction with the appended drawings. For the purposes of illustrating the device of the present application, there are shown in the drawings preferred embodiments. It should be understood, however, that the application is not limited to the precise arrangements and instrumentalities shown. In the drawings.

DETAILED DESCRIPTION

Figure 1:
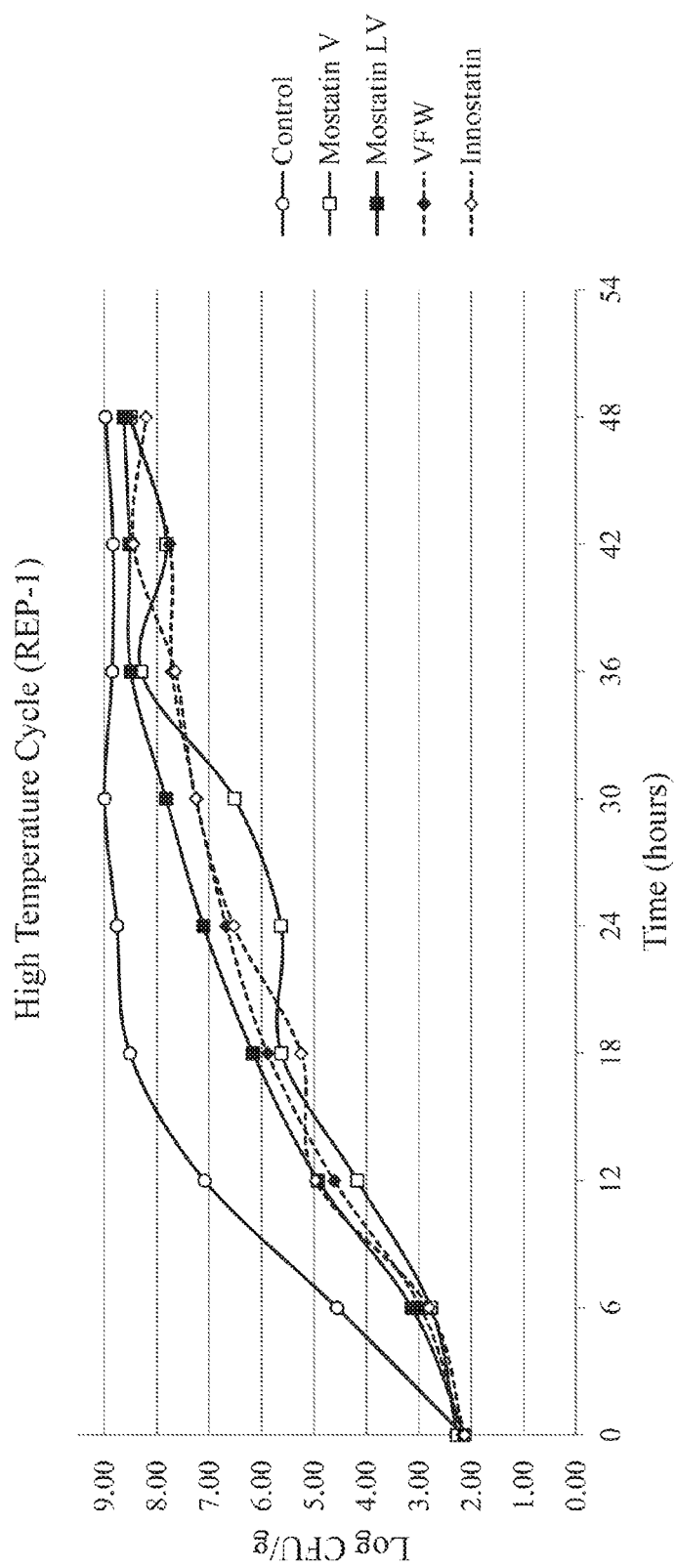
FIG. 1 shows log CFU/g of a cocktail of *Salmonella* species consisting of serotypes *S. thompson*, *S. enteritidis*, *S. hadar*, *S. montivideo* and *S. heidelberg* inoculated into comminuted chicken meat and chicken gravy containing no antimicrobial (control) or the indicated antimicrobial, and grown in an incubator with a programmed sinusoidal temperature cycling between 10 and 40° C. with 150 min/cycle.

Food processors can control foodborne pathogen levels in RTE meat and poultry products using one or more of a variety of approaches, including post-lethality treatment, antimicrobial agent(s), and sanitation measures.

Chemical agents that have been evaluated as antimicrobial agents for control of microorganisms in RTE meat and poultry products include organic acids, bioactive preservatives, and bacteriocins. Organic acids, their salts, and other agents that are commonly used in the manufacture of RTE meat products are advantageous in that they are traditional ingredients and most are designated by the U.S. Food and Drug Administration (FDA) as generally recognized as safe (GRAS).

For example, sodium and potassium salts of lactic, citric and acetic acids have been shown to provide listeriostatic effect in RTE meat products. USDA-FSIS has approved these agents for use in RTE meat and poultry products at concentrations not exceeding 4.8% for sodium or potassium lactate and 0.25% of sodium diacetate by weight of total formulation. These agents have been shown to be effective in controlling *Listeria* growth on RTE meat and poultry products and synergistic anti-listerial activity has been reported.

The growing demand for natural and organic foods from consumers has resulted in a search for natural antimicrobials for use in meat and poultry products. Lemon juice and vinegar, the natural sources of citric acid and acetic acid, respectively, or their salts (sodium or potassium) likely have inhibitory effect on the growth of foodborne pathogens. However, their juices are not preferred in meat and poultry products because of the accompanying undesirable organoleptic property changes and/or protein denaturation resulting in reduced binding of meat matrix. Nevertheless, buffered counterparts of organic acids or their salts can be used with minimal impact on meat quality. Advantageously, buffered vinegar or lemon juice and vinegar combination, if used at optimized concentrations, can provide antimicrobial activity and can supplement the available antimicrobial agents for control of pathogens in natural RTE meat and poultry products.

In preferred embodiments, the present invention provides a microbiocidal mixture comprising one or more natural antimicrobial agents such as organic acids and/or their salts and one or more essential oils. In some embodiments, the essential oils are selected fractions of vegetable essential oils. The essential oils are believed to enhance the permeability of the cell wall membrane, advantageously enabling the microbiocidal agents to rapidly enter the cell and disrupt the metabolic processes occurring inside the cell, leading to cell death.

Essential oils useful in the invention may be obtained by various methods. In some embodiments, the essential oil fractions are obtained from plant materials, such as herbs, spices, citrus peel, or a combination thereof. For example, in preparing the mixture, commercially available stock of plant derived essential oil may be fractionated by vacuum fractional distillation. From each raw essential oil stock, a fraction that condenses at a designated temperature range is condensed and recovered. In some embodiments, use of specific fractions rather than the complete oils allows the use of lower effective concentrations of the oil fractions in the treated food product, thus avoiding the strong spice flavor from the other components of the original plant oil. Illustrative fractions of essential oils useful in the invention are noted below in the Examples.

In some embodiments, a microbiocidal mixture according to the present invention includes caprylic acid, a $C_8$ fatty acid with a 7-carbon alkyl group attached to the carboxylic acid group in the molecule. Caprylic acid has demonstrated antimicrobial properties and can also promote the attachment of antimicrobial agents in the mixture to the cell wall.

The hydrophobic $C_7$ alkyl group is attracted to the lipid component of the bacterial cell wall, while the hydrophilic acid group attracts the water-miscible antimicrobial agents in the mixture. In some embodiments, caprylic acid can promote substantially uniform distribution of the essential oil fractions in the antimicrobial mixture, thereby producing a homogeneous system that avoids separation of the essential oil fractions during storage.

In some embodiments, the invention provides an antimicrobial mixture comprising two or more antimicrobial organic acids. In some embodiments, the invention provides an antimicrobial mixture comprising levulinic acid and malic acid. These two acids can synergistically interact with the essential oil fractions and caprylic acid to accelerate killing of Gram negative pathogenic bacteria, such as *Salmonella*, *E. coli* 0157:H7 and other pathogenic *E. coli* strains. Embodiments of the present invention are also effective to accelerate killing and/or prohibiting growth of Gram positive bacteria, such as *L. monocytogenes*.

In some embodiments, the invention provides an antimicrobial mixture comprising a mixture of a mineral salt of malic acid with the acid itself in a ratio that raises the pH of the malic acid component in the mixture to about 5.2, the pKa of the second carboxylic group of the acid. Buffering the acid advantageously eliminates a sour taste in the product to which the antimicrobial agent is added and avoids denaturation of proteins in the product.

The microbiocidal mixtures described herein may be applied according to various processes. In some embodiments, a microbiocidal mixture described herein is sprayed on whole carcasses of small birds, primal cuts of large animals, cut-up bone-in parts of turkey prior to further processing as ready to cook raw products or mechanically deboned or comminuted to produce ground processed meats. In some embodiments, a microbiocidal mixture described herein is added to ready to cook raw meat or ground mechanically deboned meat in a mixer or tumbler to homogeneously incorporate the mixture into the meat.

EXAMPLES

Example 1

In the tests shown in FIGS. 1-4 the substrate to be inoculated was a commercial product, thermally processed jars of baby food, Chicken and Chicken Gravy. Ground chicken was aseptically transferred from the baby food jars into a plastic bag and an antimicrobial was added in an amount that would yield the desired concentration of 1% of meat weight. The antimicrobial was dispersed homogeneously into the meat by kneading the plastic bag after addition of the antimicrobial. Approximately 20 g of the ground meat with the antimicrobial was then transferred into each of several small plastic bags and each bag was inoculated with the test organism. After inoculation each bag was kneaded to disperse the inoculum uniformly in the meat. The inoculum was actively growing cells of a cocktail of *Salmonella* spp. consisting of the following serotypes: *S. thompson, S. enteritidis, S. hadar, S. montivideo* and *S. heidelberg*. The bags were then incubated in an incubator with a programmed oscillating temperature. The high temperature range was 10 to 40° C. with 150 min/cycle. The low temperature range was 5 to 15° C. with 180 min/cycle. One bag of each sample was removed at designated times of incubation and viable organisms in each bag were enumerated using standard plating techniques.

Figure 5:
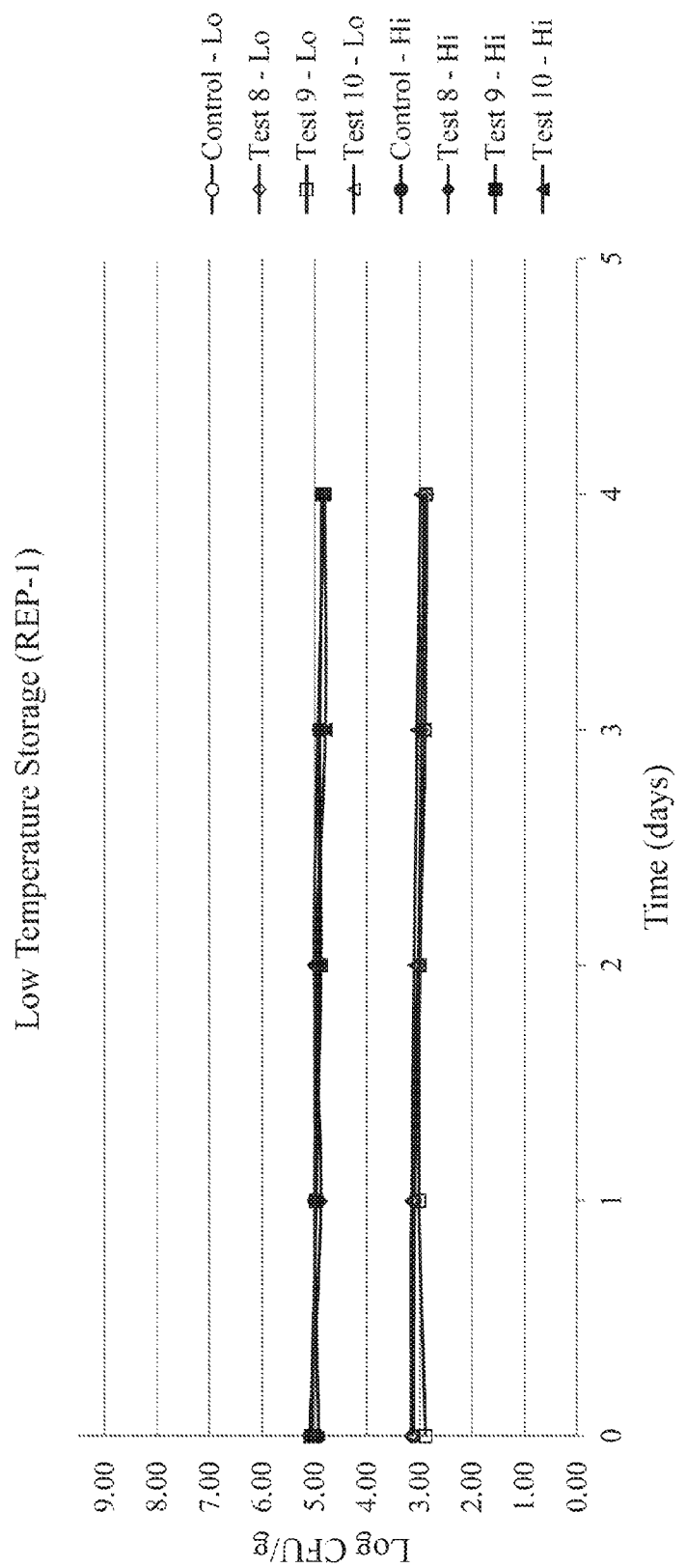
FIG. 5 shows log CFU/g of a cocktail of *Salmonella* species consisting of serotypes *S. thompson, S. enteritidis, S. hadar, S. montivideo* and *S. heidelberg* inoculated into raw ground turkey meat and grown in an incubator maintained at a constant temperature of 5° C. Hi represents inoculating the *Salmonella* cocktail at 5 log CFU/g, and Lo represents inoculating the cocktail at 3 CFU/g.
Figure 6:
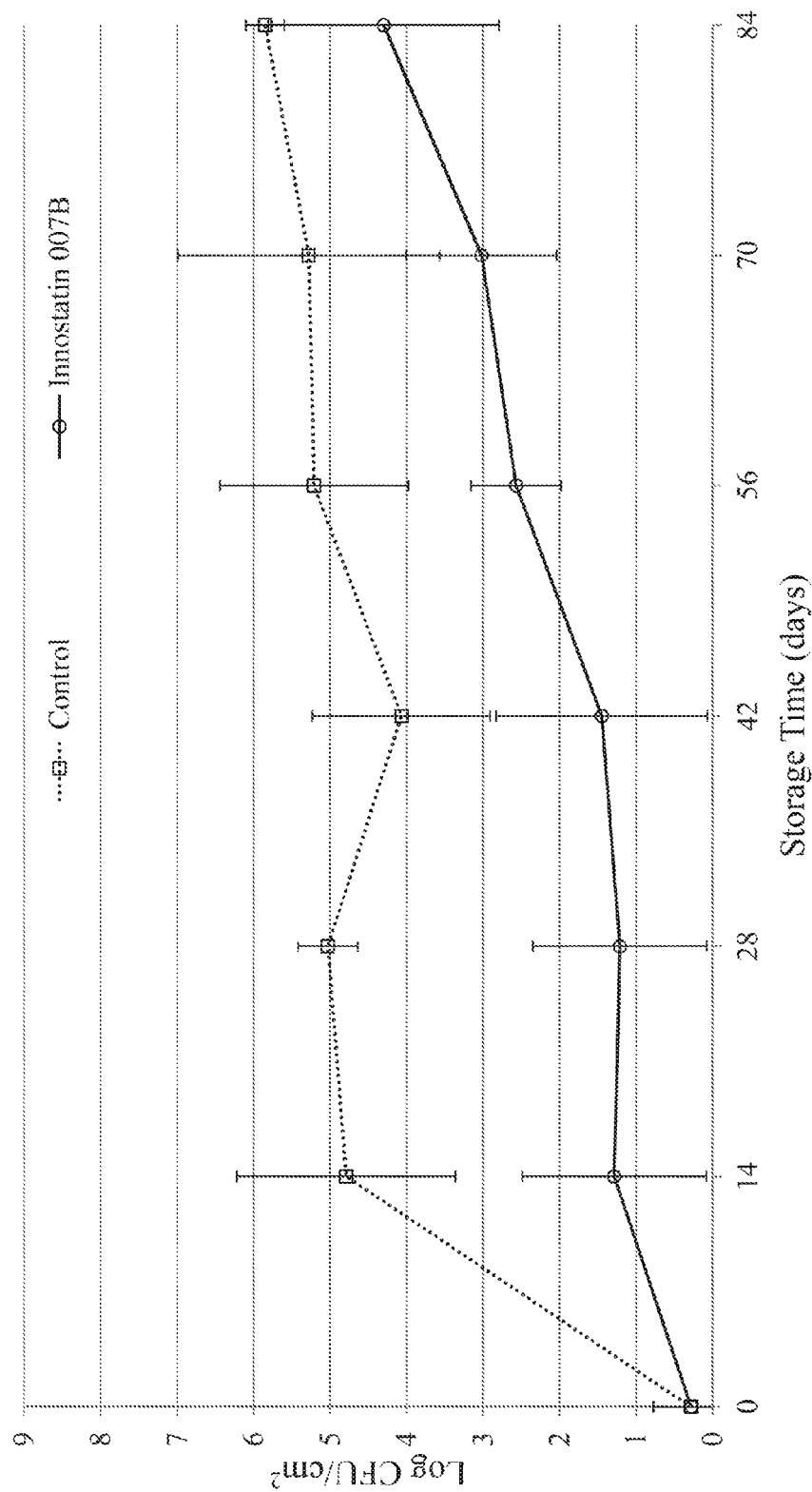
FIG. 6 shows Mean Aerobic Plate Counts of turkey loaves containing natural antimicrobial agent (Innostatin 007B at 2% concentration in formulation) and control (no antimicrobial) during refrigerated, vacuum storage at 4.4° C.
Figure 7:
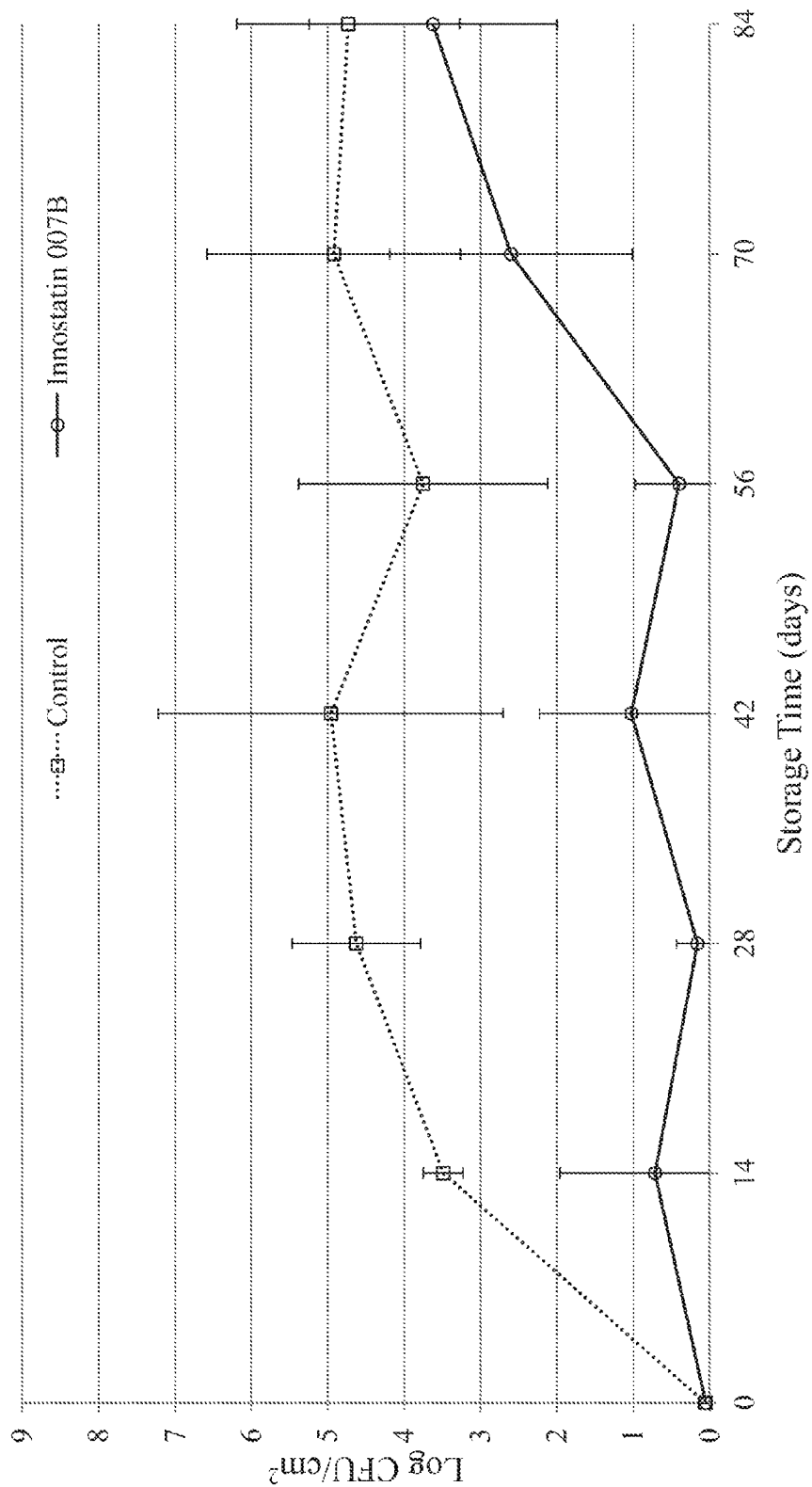
FIG. 7 shows Mean Psychrotrophic Plate Counts of turkey loaves containing natural antimicrobial agent (Innostatin 007B at 2% concentration in formulation) and control (no antimicrobial) during refrigerated, vacuum storage at 4.4° C.
Figure 8:
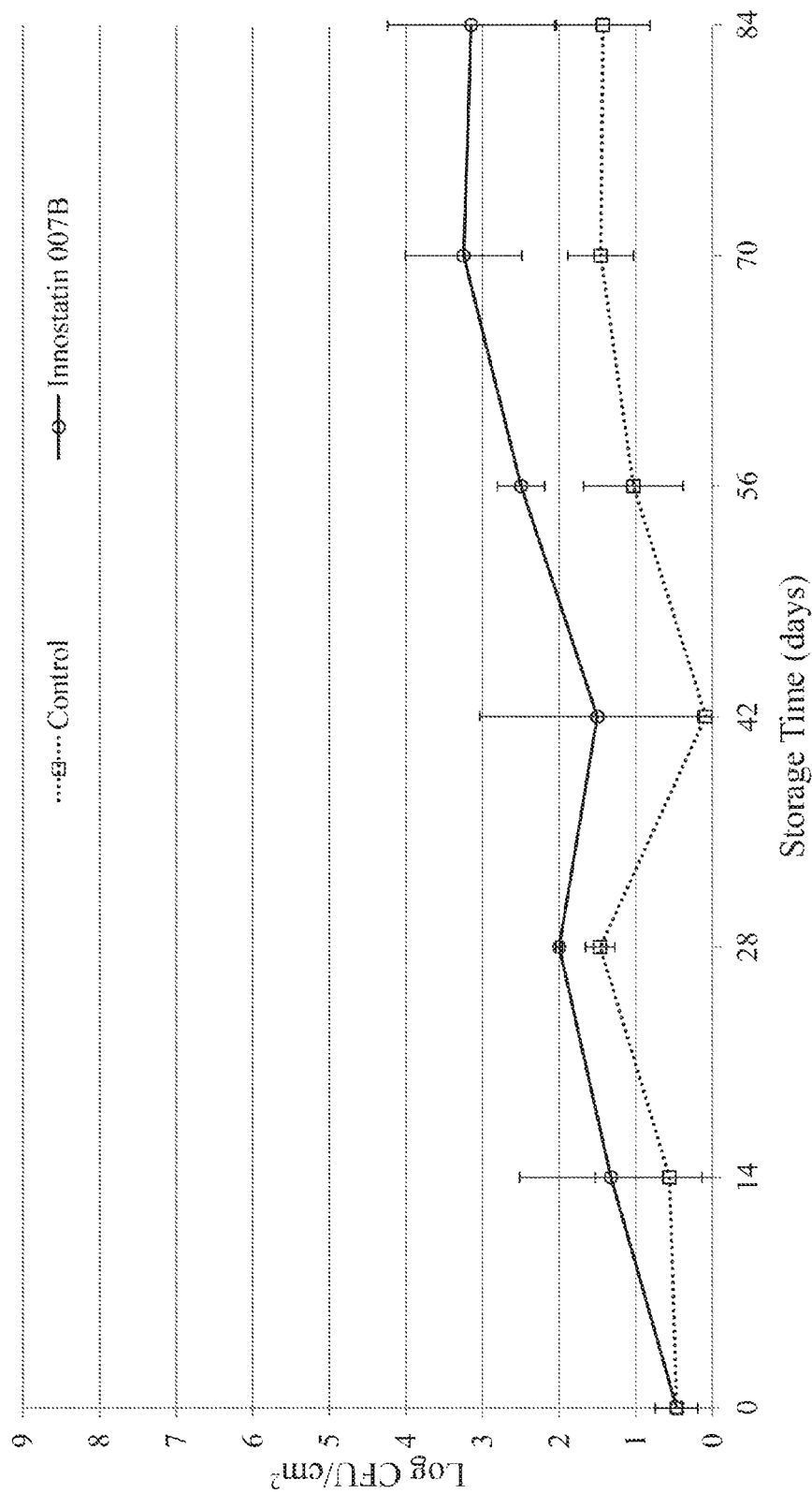
FIG. 8 shows Mean Yeast and Mold Counts of turkey loaves containing natural antimicrobial agent (Innostatin 007B at 2% concentration in formulation) and control (no antimicrobial) during refrigerated, vacuum storage at 4.4° C.
Figure 9:
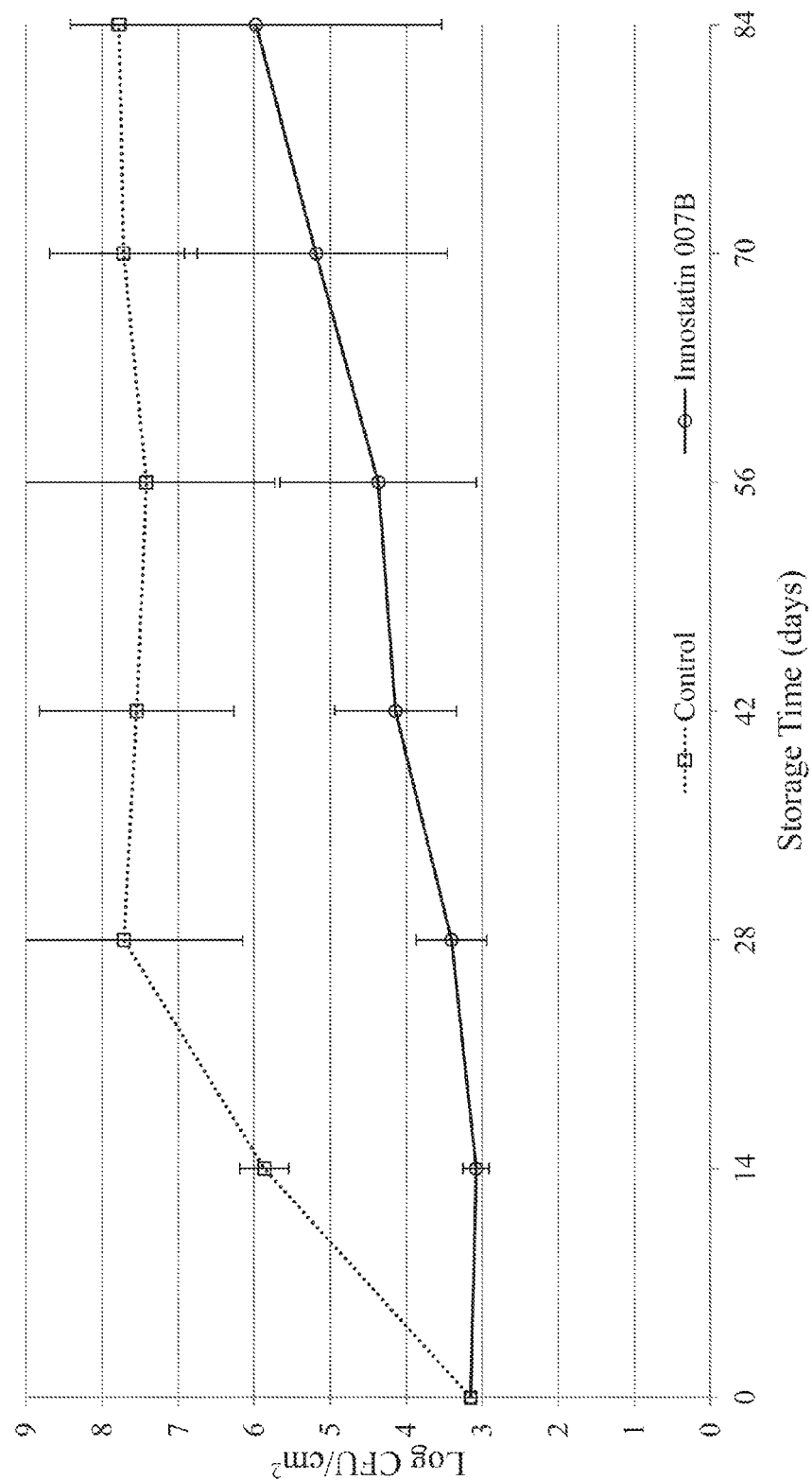
FIG. 9 shows Mean *Listeria monocytogenes* populations of turkey loaves (inoculated with the organism) containing natural antimicrobial agent (Innostatin 007B at 2% concentration in formulation) and control (no antimicrobial) during refrigerated, vacuum storage at 4.4° C.
Figure 10:
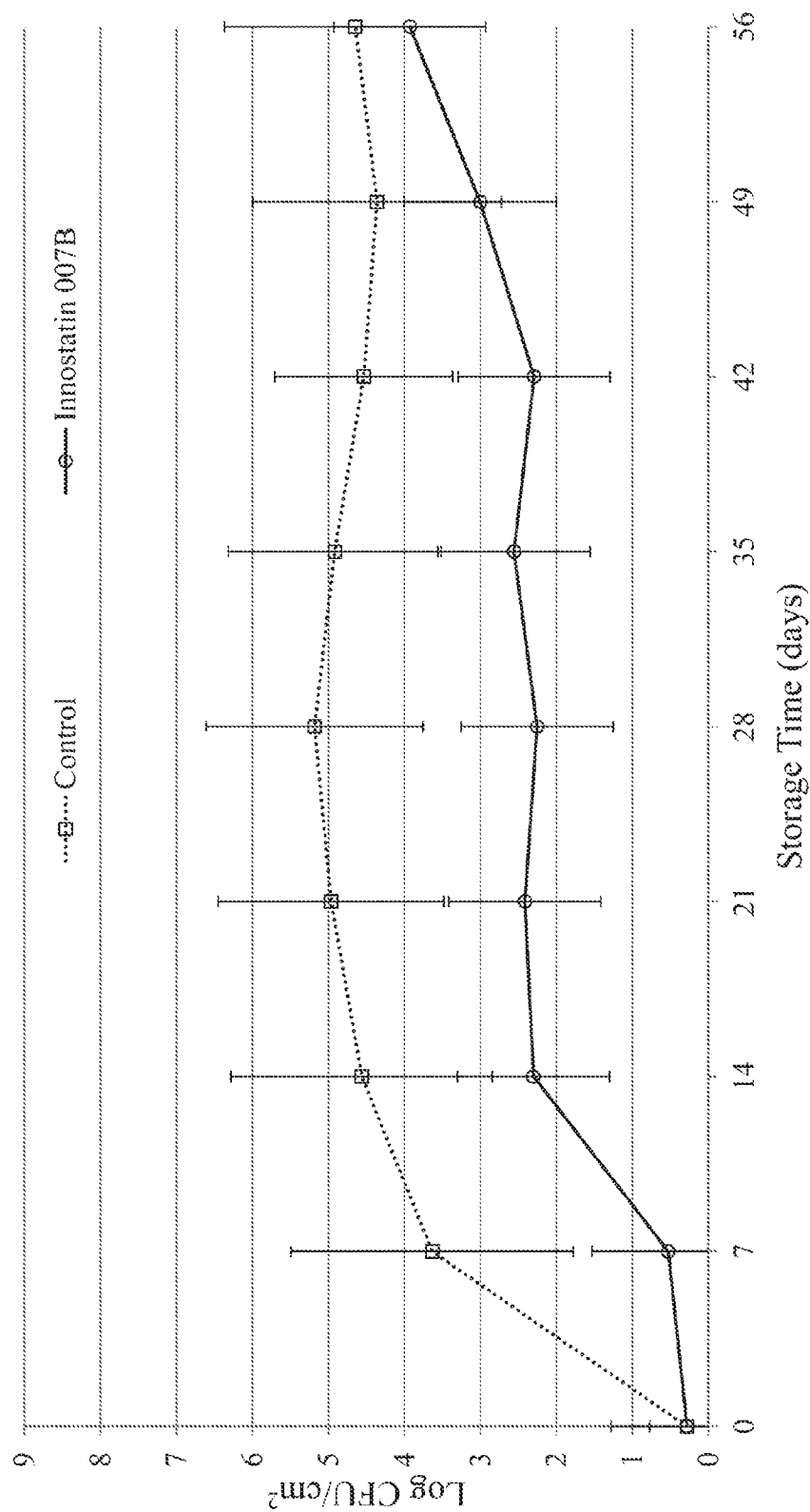
FIG. 10 shows Mean Aerobic Plate Counts of turkey loaves containing natural antimicrobial agent (Innostatin 007B at 2% concentration in formulation) and control (no antimicrobial) during refrigerated, vacuum storage at 10° C.
Figure 11:
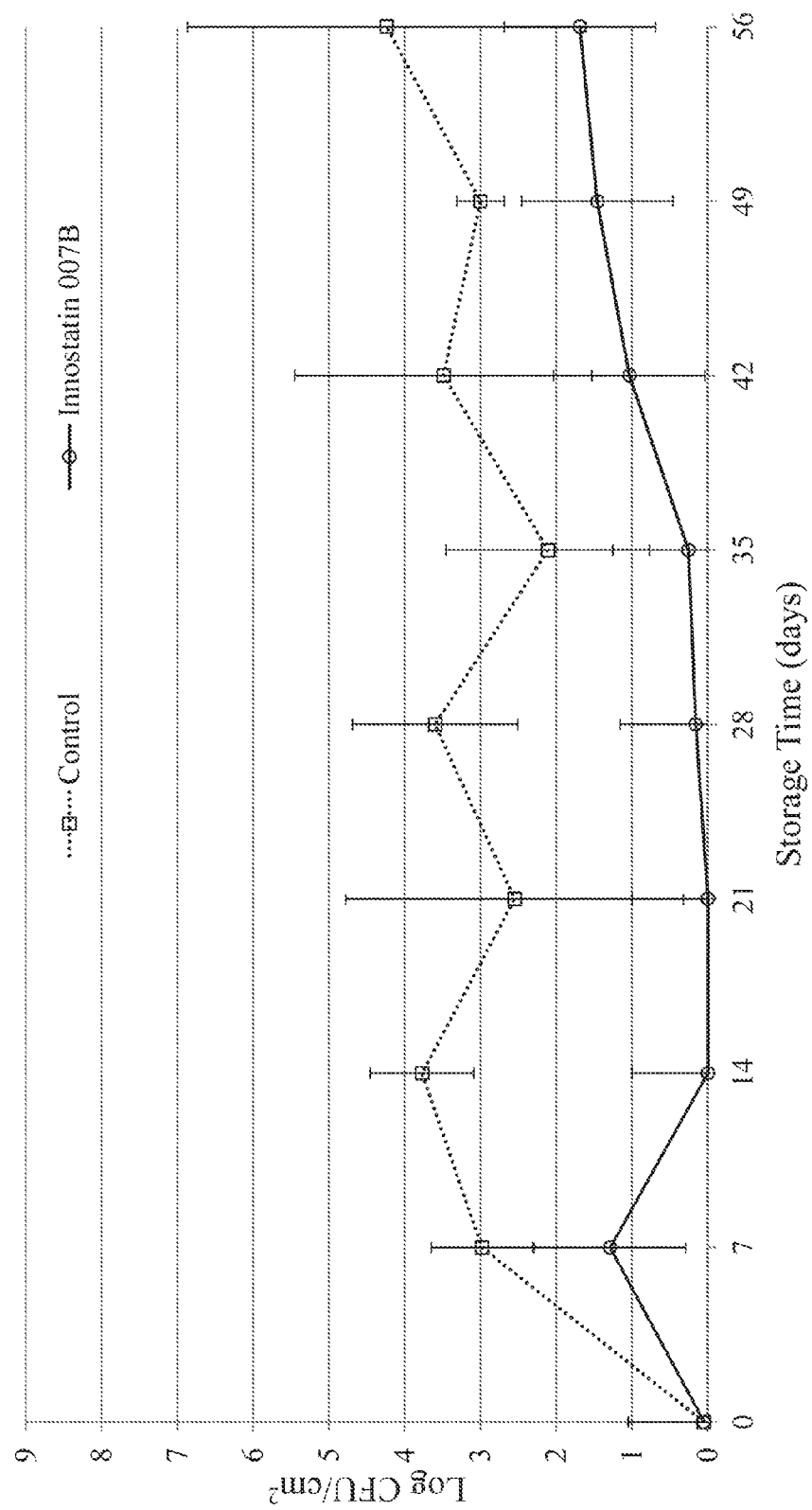
FIG. 11 shows Mean Psychrotrophic Plate Counts of turkey loaves containing natural antimicrobial agent (Innostatin 007B at 2% concentration in formulation) and control (no antimicrobial) during refrigerated, vacuum storage at 10° C.
Figure 12:
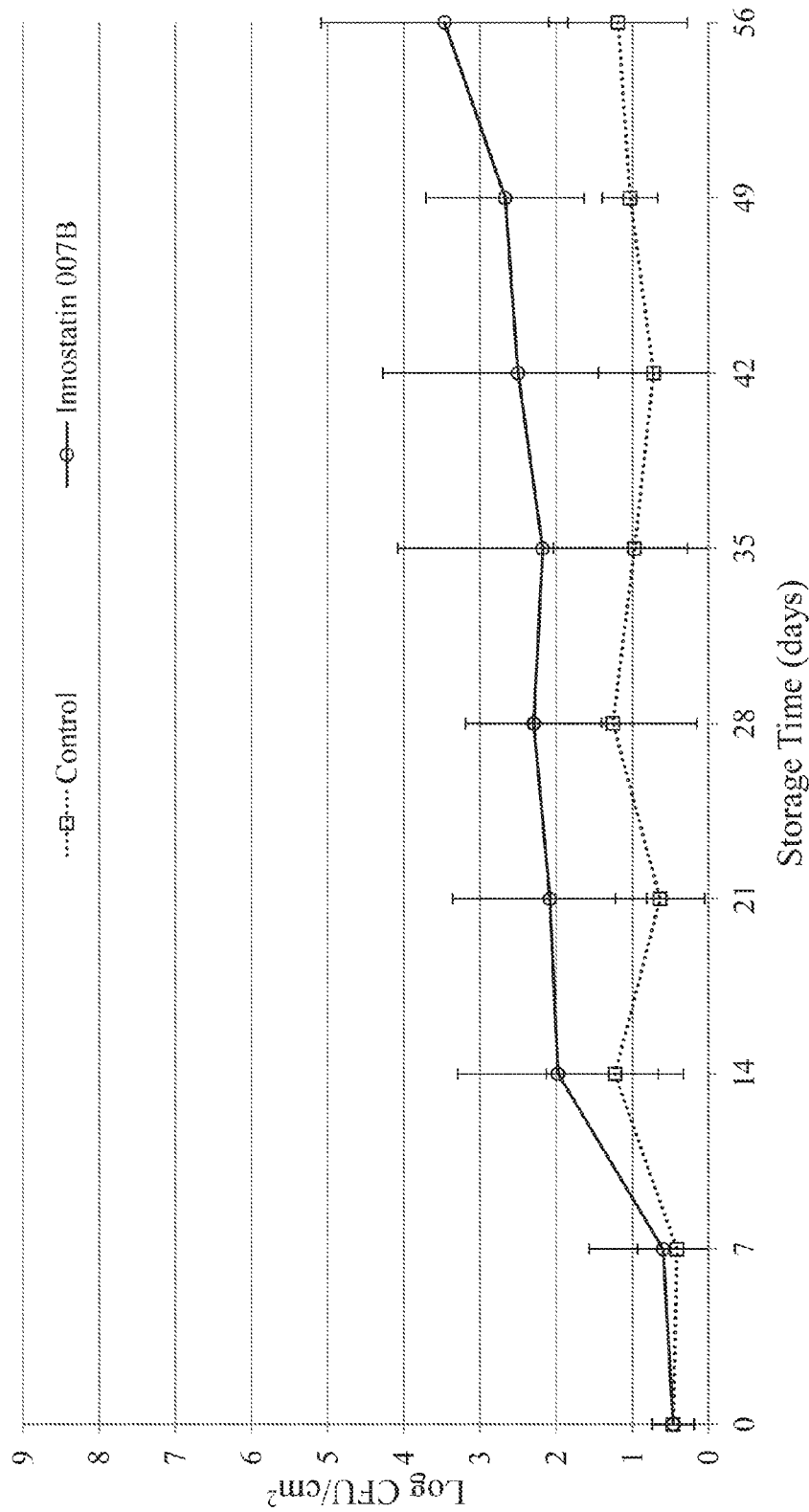
FIG. 12 shows Mean Yeast and Mold Counts of turkey loaves containing natural antimicrobial agent (Innostatin 007B at 2% concentration in formulation) and control (no antimicrobial) during refrigerated, vacuum storage at 10° C.
Figure 13:
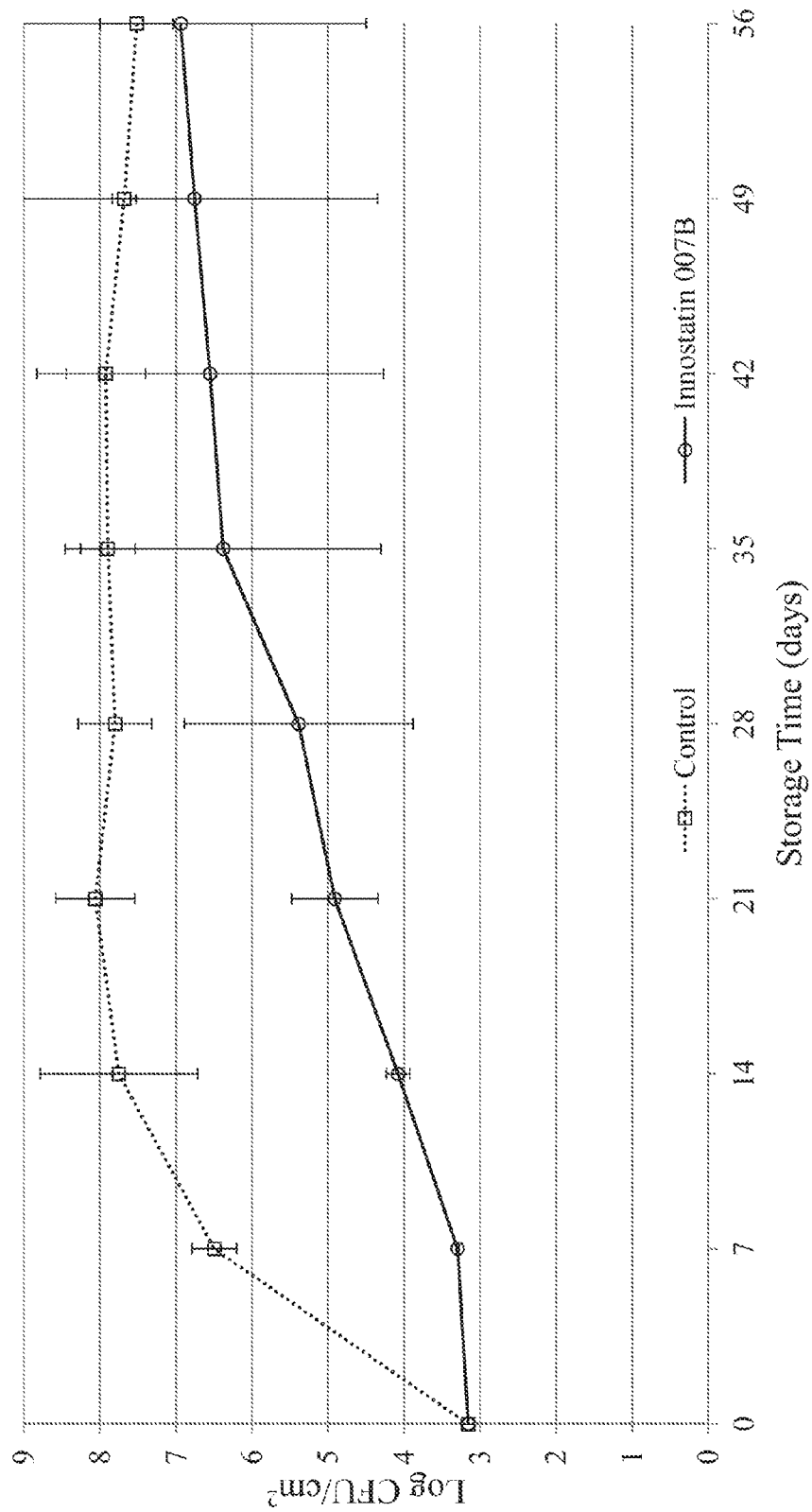
FIG. 13 shows Mean *Listeria monocytogenes* populations of turkey loaves (inoculated with the organism) containing natural antimicrobial agent (Innostatin 007B at 2% concentration in formulation) and control (no antimicrobial) during refrigerated, vacuum storage at 10° C.

The test shown in FIG. 5 involved treated ground raw turkey meat (unsterilized prior to inoculation) inoculated with the same *Salmonella* spp. cocktail as used in the tests shown in FIGS. 1-4 and stored at 5° C. constant temperature. The Hi and Lo caption in FIG. 5 indicates the level of inoculum of about 5 log CFU/g and 3 log CFU/g, respectively.

All antimicrobials (microbiocidal mixtures) were pre-blended and supplied as a ready-to-use mix. All antimicrobials were used at the 1% level in the meat, although different concentrations may be used. For example, in applications where it is desirable to reduce the taste of the essential oil fractions, such as ready-to-eat meats, the concentration of the essential oils may be reduced (e.g., from 200 to 100 micrograms/L of each of Fractions C and L) and the antimicrobial mixture at a different level (e.g., 2%, not 1%, in the meat).

FIGS. 1-5 are graphical representations of the results of various screening tests, in which the following mixtures were used:

Control: Chicken meat puree alone, no antimicrobial, inoculated with *Salmonella* spp. cocktail MOstatin V: Concentrated buffered vinegar (e.g., described in U.S. Pat. No. 8,182,858, hereby incorporated herein by reference), comprising buffered vinegar that has been concentrated by evaporation to produce an elevated acetate concentration of 34 to 38% acetate salts and a free acetic acid content of 3.5 to 4.5% by weight MOstatin LV: A mixture comprising equal parts of neutralized lemon concentrate and buffered vinegar concentrate VFB (referred to as VFW in the Figures): Mix of 50% MOstatin V and 50% buffered unconcentrated vinegar Innostatin 007 (referred to as Innostatin in the Figures): VFB containing 200 micrograms each of essential oil Fraction C and essential oil Fraction L per gram VFB; when used at the 1% level in the marinated meat, the concentrations of essential oil Fractions C and L were each 2 micrograms per gram of meat Test 8 Mixture: 0.3% Innostatin 007; 0.3% Levulinic Acid; 0.3% Malic Acid; and 0.1% Water Test 9 Mixture: Innostatin 007

Test 10 Mixture: 0.45% Levulinic Acid; 0.45% Malic Acid; 0.1% Water; and 200 ppm each of essential oil Fraction C and essential oil Fraction L Essential oil Fraction C is a fraction from oil of Turkish oregano, which condenses at 103 to 120° C. at an absolute pressure of 10 mm Hg. This fraction consists primarily of Carvacrol (IUPAC name 5-isopropyl-2methylphenol).

Essential oil Fraction L is a fraction from orange oil, which condenses at 60 to 80° C. at an absolute pressure of 10 mm Hg. This fraction consists primarily of Linalool (IUPAC name 3,7-dimethylocta-1,6-dien-3-ol).

Figure 2:
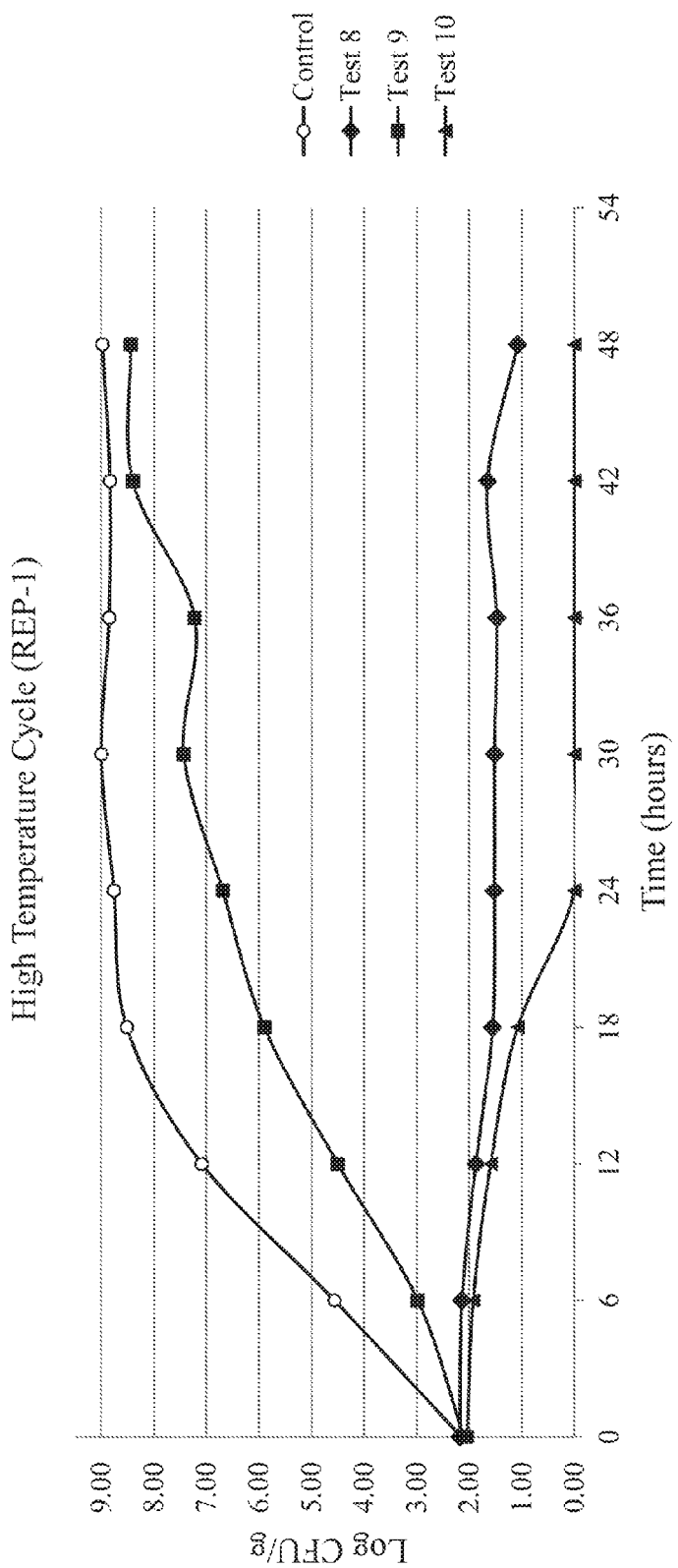
FIG. 2 shows log CFU/g of a cocktail of *Salmonella* species consisting of serotypes *S. thompson*, *S. enteritidis*, *S. hadar*, *S. montivideo* and *S. heidelberg* inoculated into comminuted chicken meat and chicken gravy containing no antimicrobial (control) or the indicated antimicrobial, and grown in an incubator with a programmed sinusoidal temperature cycling between 10 and 40° C. with 150 min/cycle.
Figure 3:
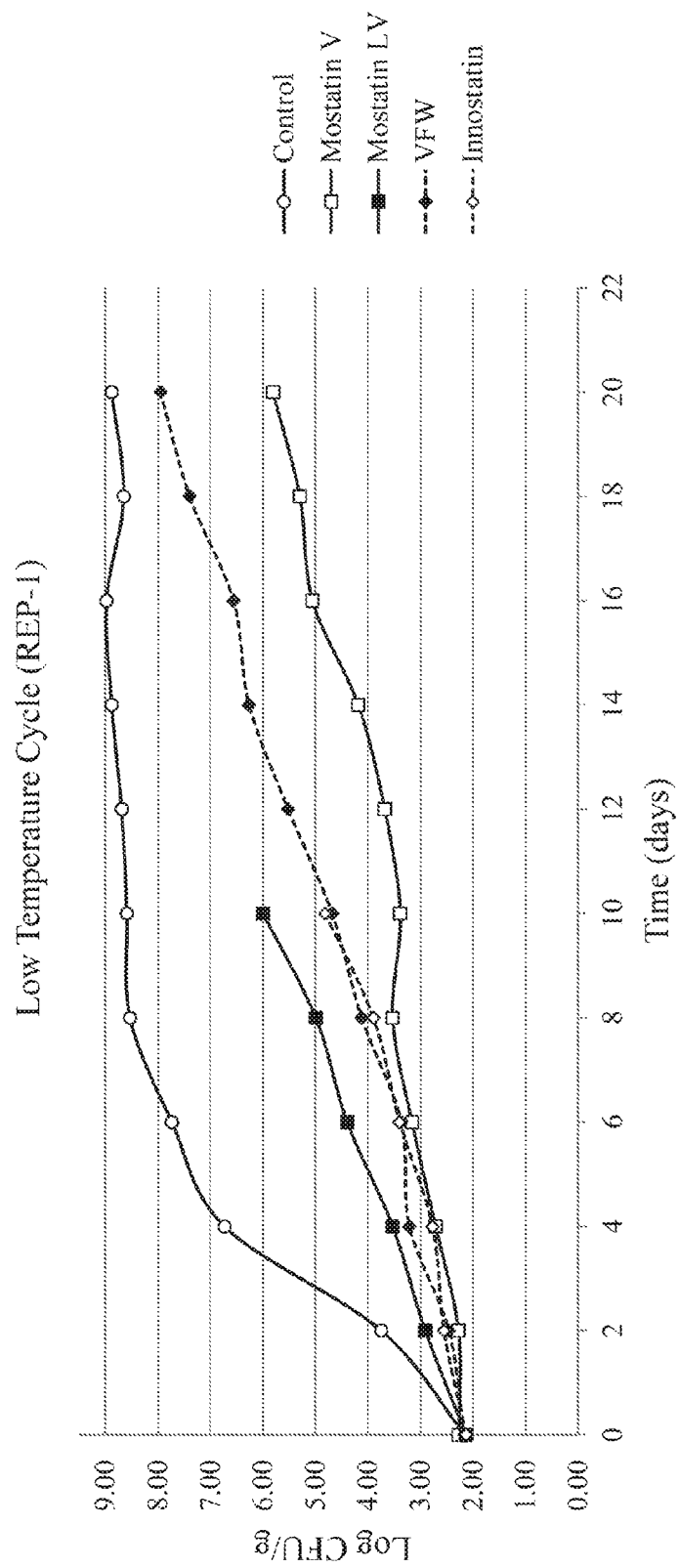
FIG. 3 shows log CFU/g of a cocktail of *Salmonella* species consisting of serotypes *S. thompson, S. enteritidis, S. hadar, S. montivideo* and *S. heidelberg* inoculated into comminuted chicken meat and chicken gravy containing no antimicrobial (control) or the indicated antimicrobial, and grown in an incubator with a programmed sinusoidal temperature cycling between 5 and 15° C. with 180 min/cycle.
Figure 4:
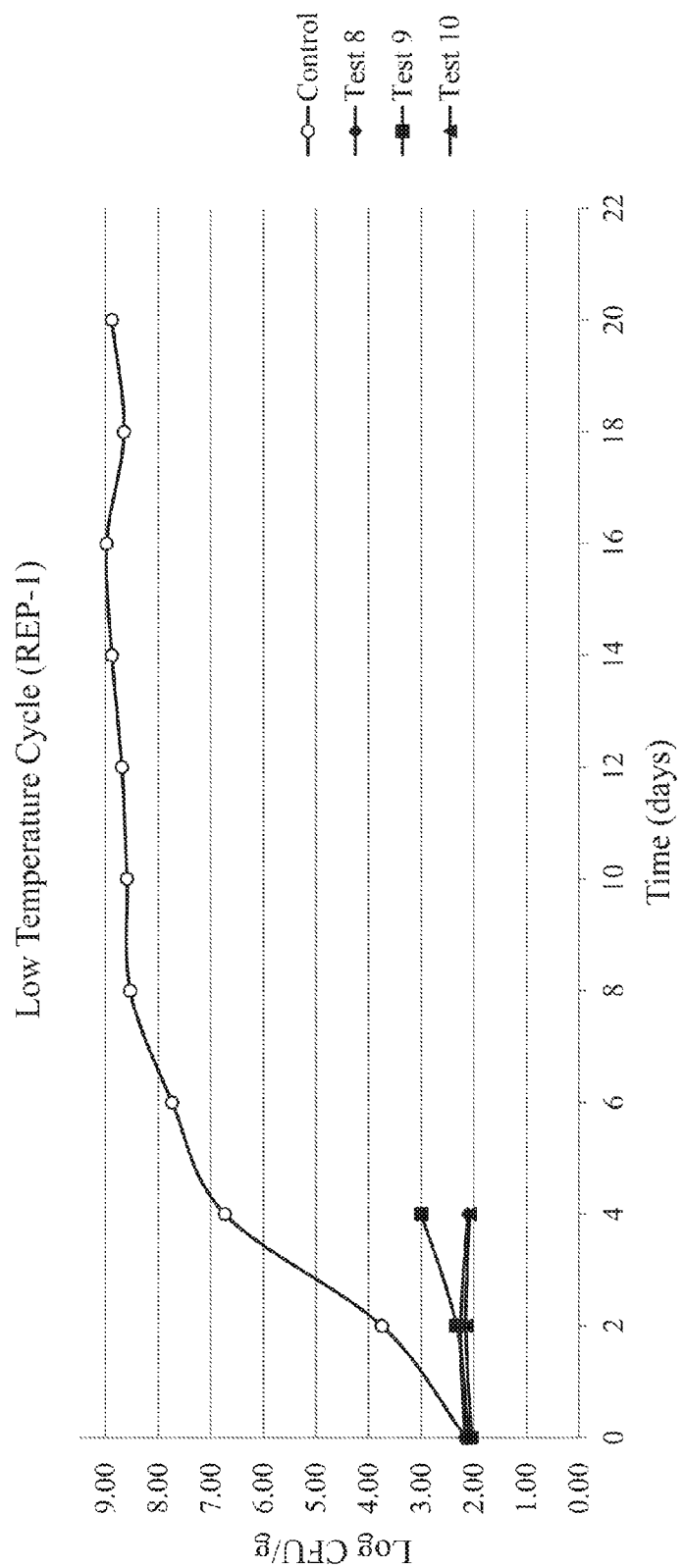
FIG. 4 shows log CFU/g of a cocktail of *Salmonella* species consisting of serotypes *S. thompson, S. enteritidis, S. hadar, S. montivideo* and *S. heidelberg* inoculated into comminuted chicken meat and chicken gravy containing no antimicrobial (control) or the indicated antimicrobial, and grown in an incubator with a programmed sinusoidal temperature cycling between 5 and 15° C. with 180 min/cycle.

As will be easily appreciated by those of skill in the art based on FIG. 2, the Test 10 Mixture and, to a lesser extent, the Test 8 Mixture, not only inhibit the growth of, but also kill, the pathogenic microorganisms.

Example 2

This Example describes tests for inhibition of spoilage bacteria in raw chicken.

In the test shown in Table 1, the product was chicken drumsticks tumble marinated with a marinade that would yield the following concentrations in the marinated product after absorption of 15% of the marinade:

Control: Chicken marinated to yield 0.8% salt and 0.5% phosphate

Treatment A: Sodium tripolyphosphate 0.5%, salt 0.8%, and 1.5% VFB containing 1.5 micrograms of essential oil Fraction L per gram VFB and 0.75 micrograms of essential oil Fraction C per gram VFB; concentrations of essential oils in marinated product are 0.113 micrograms/g of essential oil Fraction C and 0.225 micrograms/g of essential oil fraction L Treatment B: Chicken marinated to yield 0.8% salt, 0.5% phosphate, and 1.5% VFB; no essential oil

TABLE 1

| TIME (from inoculation) | Control Aerobic Plate Count (APC) (cfu/gram) | A APC (cfu/gram) | B APC (cfu/gram) |
|---|---|---|---|
| Initial | 100,000 | 39,000 | 41,000 |
| Day 4 | 470,000 | 45,000 | 59,000 |
| Day 7 | 1,600,000 | 98,000 | 130,000 |
| Day 10 | 2,300,000 | 290,000 | 350,000 |
| Day 13 | 4,500,000 | 570,000 | 610,000 |
| Day 16 | 8,000,000 | 980,000 | 1,200,000 |
| Day 19 | 12,000,000 | 1,300,000 | 1,500,000 |

In the test shown in Table 2, the product was boneless skinless chicken breast strips tumble marinated with a marinade that would yield the following concentrations in the marinated product after absorption of 15% of the marinade:

Treatment A: Chicken marinated to yield 0.8% salt, 0.5% phosphate, and 1.5% VFB; no essential oil Treatment B: Sodium tripolyphosphate 0.5%, salt 0.8%; and 1.5% VFB containing 100 micrograms of essential oil Fraction L per gram VFB and 50 micrograms of essential oil Fraction C per gram VFB; concentrations of essential oils in marinated product are 7.5 micrograms/g of essential oil Fraction C and 15 micrograms/g of essential oil Fraction L

TABLE 2

| TIME (from inoculation) | A APC (cfu/gram) | B APC (cfu/gram) |
|---|---|---|
| Initial | 33,000 | 28,000 |
| Day 4 | 40,000 | 36,000 |
| Day 8 | 85,000 | 78,000 |
| Day 12 | 150,000 | 130,000 |
| Day 16 | 270,000 | 190,000 |
| Day 20 | 1,800,000 | 230,000 |
| Day 24 | 2,300,000 | 510,000 |

In the test shown in Table 3, the product was ground chicken breast meat. Several concentrations of essential oils in VFB were prepared to give different concentrations of the essential oils when mixed in the meat at the 1% level of addition. Equal concentrations of essential oil Fraction C and essential oil Fraction L were used. Table 3 shows the results of the following treatment:

Treatment A: Innostatin 007

TABLE 3

| TIME (from inoculation) | CONTROL APC (cfu/gram) | A APC (cfu/gram) |
|---|---|---|
| Initial | 27,000 | 23,000 |
| Day 3 | 50,000 | 35,000 |

TABLE 3-continued

| TIME (from inoculation) | CONTROL APC (cfu/gram) | A APC (cfu/gram) |
|---|---|---|
| Day 6 | 90,000 | 80,000 |
| Day 9 | 170,000 | 110,000 |
| Day 15 | 2,000,000 | 260,000 |
| Day 18 | N/T | 490,000 |
| Day 21 | N/T | 540,000 |
| Day 24 | N/T | 600,000 |
| Day 27 | N/T | 770,000 |

Example 3

A five-strain cocktail of *Listeria monocytogenes* [101M, 109, 108M, serotype 4c American Type Culture Collection (ATCC), and serotype 3 ATCC] was used for inoculation of the RTE non-cured turkey breast product. The cultures were maintained separately on Tryptic Soy Agar (TSA; Difco, Detroit, Mich.) slants at 4° C. The inoculum was prepared by inoculating the cultures into 10 ml Tryptic Soy Broth (TSB; Difco, Detroit, Mich.) and incubating at 35° C. for 24 h. Fresh cultures (1 ml) were transferred into 10 ml TSB and incubated at 35° C. for 20 h. A mixed strain culture-cocktail was prepared by mixing equal proportions of the five strains in a sterile container to obtain approximately equal populations of each strain in the inoculum.

Products were formulated and prepared in a meat processing facility, chilled and shipped to the testing laboratories under refrigeration. On arrival, the products were transferred to a cooler set at 4.4° C. and stored until use. On each day of inoculation for each replication, appropriate number of each product type were opened, sliced in a USDA-FSIS inspected facility, and inoculated as described below. Two treatments, control (without any antimicrobials) and Innostatin 007B (2%) were used. Product formulations (%) of turkey loaf containing natural antimicrobial agent Innostatin 007B are shown in Table 4. Innostatin 007B is Innostatin 007 formulated for use at 2%. Innostatin 007B contains half the amount each of essential oil Fraction C and essential oil Fraction L per gram VFB, as compared to Innostatin 007; when used at the 2% level in the marinated meat, the concentrations of essential oil Fractions C and L are each 2 micrograms per gram of meat. Each test variable was produced in 40 lb batches.

TABLE 4

| | CONTROL | Innostatin 007B |
|---|---|---|
| Skinless, Boneless Turkey Breast Meat | 76.92 | 76.92 |
| Water/Ice | 19.48 | 17.48 |
| Salt Granular | 1.75 | 1.75 |
| Cane Sugar | 1.50 | 1.50 |
| Innostatin 007B | 0 | 2.00 |
| TOTAL | 100 | 100 |

The product slices were inoculated using a template in a biosafety cabinet. The inoculated slice was placed between two non-inoculated slices to replicate postprocess contamination with *L. monocytogenes* during slicing operation. The products were vacuum packaged and thermally sealed using a Multivac packaging system and stored at either 4.4° C. or 10° C. Each of the products were removed from the cooler and sampled at 14 day intervals for product stored at 4.4° C. and weekly for product stored at 10° C.

The product was aseptically removed from the package and placed on an alcohol sterilized metal surface. Product surface samples were obtained using a sterile, stainless steel core (a total of 21.2 cm$^2$), transferred to a stomacher bag, diluted with 50 ml of 0.1% sterile PW. The samples were homogenized in a Stomacher blender (Neutec, Albuquerque, NM) for two minutes. Samples were serially diluted in sterile PW and spiral plated onto Modified Oxford Agar (MOX; Oxoid Ltd., Basingstoke, Hampshire, England) using a spiral plater or by spread plating. The plates were incubated at 35° C. for 48 h and typical colonies were enumerated manually using a spiral plate dark field Quebec colony counter (Model 330; American optical company, Buffalo, N.Y.). Counts were recorded as log Colony Forming Units per sq. cm. ($\log_{10}$ CFU/cm$^2$) of the product.

The pH of the turkey loaves were 5.95 and 5.84, respectively for control and product containing Innostatin 007B (2%). The water activity of the turkey loaves was 0.976 for all the treatments, Control, turkey loaf containing Innostatin 007B.

Initial Aerobic Plate Counts (APCs), Psychrotrophic Counts (PCs) and Yeast and Mold (Y&M) counts of 0.28, 0.05 and 0.47 log CFU/cm$^2$ were observed on non-inoculated turkey loaves (control), respectively. Storage of turkey loaves (control) at 4.4° C. resulted in APCs of >4.51 log CFU/cm$^2$ within 14 days, while the populations were lower in the product containing Innostatin 007B, with 2.74 log CFU/cm$^2$ on day 70. Greater increases in APCs were observed in product stored at 10° C., with populations of 4.28 log CFU/cm$_2$ reaching within 14 days of storage in control turkey loaf. The APCs of turkey loaves containing Innostatin 007B (2%) were 3.65 log CFU/cm$^2$ after 56 days of storage. The psychrotrophic plate counts followed similar trend as the TPCs, for all the products, with turkey loaves containing Innostatin 007B showing lower populations compared to the control product at respective storage times and temperatures.

*L. monocytogenes* population of 3.15 log CFU/cm$^2$ (mean) was obtained subsequent to inoculation on all the products. Refrigerated storage of the turkey loaves (control) at 4.4° C. resulted in *L. monocytogenes* population increases of 2.71 and 4.56 log CFU/cm$^2$ by day 14 and 28, respectively, with the populations stabilizing after 28 days at final populations of ca. 7.5 log CFU/cm$^2$. Incorporation of Innostatin 007B (2%) in turkey loaf formulation resulted in inhibition of *L. monocytogenes* population, with increases of 0.0, 0.25, 0.99, 1.22, 2.04, and 2.83 log CFU/cm$^2$ by 14, 28, 42, 56, 70 and 84 days of storage at 4.4° C., respectively.

The mean *L. monocytogenes* population increases by ≥2.0 log CFU/cm$^2$ occurred within 14 days and >56 days on control turkey loaves, and turkey loaves containing Innostatin 007B (2%), respectively when stored at 4.4° C.

Storage of turkey loaves at abusive temperature of 10° C. resulted in faster growth of *L. monocytogenes*, with populations reaching >2.0 log CFU/cm$^2$ within 7 days and 28 days, on control turkey loaves and turkey loaves containing Innostatin 007B (2%), respectively.

While there have been shown and described fundamental novel features of the invention as applied to the preferred and exemplary embodiments thereof, it will be understood that omissions and substitutions and changes in the form and details of the disclosed invention may be made by those skilled in the art without departing from the spirit of the invention. Moreover, as is readily apparent, numerous modifications and changes may readily occur to those skilled in the art. Hence, it is not desired to limit the invention to the exact construction and operation shown and described and, accordingly, all suitable modification equivalents may be resorted to falling within the scope of the invention as claimed. It is the intention, therefore, to be limited only as indicated by the scope of the claims appended hereto.

What is claimed is:

1. A composition for treating a meat product, comprising approximately equal parts of levulinic acid and malic acid; and approximately equal parts of a first essential oil fraction and a second essential oil fraction,
    wherein the first essential oil fraction comprises the fraction which condenses from oregano oil at about 103° C. to about 120° C. at an absolute pressure of about 10 mm Hg; and
    wherein the second essential oil fraction comprises the fraction which condenses from orange oil at about 60° C. to about 80° C. at an absolute pressure of about 10 mm Hg.

2. The composition of claim 1, wherein the composition comprises about 0.45% each of the levulinic acid and the malic acid.

3. The composition of claim 1, further comprising caprylic acid.

4. The composition of claim 1, wherein the malic acid comprises a mixture of malic acid and its mineral salt in a ratio that raises the pH of the malic acid component in the mixture to about 5.2.

5. The composition of claim 1, wherein the first essential oil fraction consists essentially of 5-isopropyl-2-methylphenol (carvacrol); and the second essential oil fraction consists essentially of 3,7-dimethylocta-1,6-dien-3-ol (linalool).

6. The composition of claim 1, wherein the composition comprises about 200 ppm each of the first essential oil fraction and the second essential oil fraction.

7. The composition of claim 1, wherein the composition, when applied to the meat product, provides about 2 μg each of the first essential oil fraction and the second essential oil fraction, per gram of meat product.

* * * * *